(12) United States Patent
Ball (10) Patent No.: US 7,659,123 B2
(45) Date of Patent: Feb. 9, 2010

(54) IN SITU REMEDIAL ALTERNATIVE AND AQUIFER PROPERTIES EVALUATION PROBE SYSTEM

(75) Inventor: Raymond G. Ball, Newton, MA (US)

(73) Assignee: EnChem Engineering, Inc., Newton, MA (US)

( * ) Notice: Subject to any disclaimer, the term of this patent is extended or adjusted under 35 U.S.C. 154(b) by 795 days.

(21) Appl. No.: 10/931,012

(22) Filed: Aug. 31, 2004

(65) Prior Publication Data
US 2006/0046297 A1   Mar. 2, 2006

(51) Int. Cl.
*G01N 33/00* (2006.01)
(52) U.S. Cl. .............................. 436/28; 422/50; 422/55; 422/58; 422/68.1; 422/99
(58) Field of Classification Search .................... 436/28; 422/50, 55, 58, 68.1, 99
See application file for complete search history.

(56) References Cited

U.S. PATENT DOCUMENTS

| 5,487,431 | A | 1/1996 | Webb |
| 5,501,802 | A | 3/1996 | Thorp et al. |
| 5,548,991 | A | 8/1996 | Ritson |

(Continued)

OTHER PUBLICATIONS

Drever, J.I., et al., "The Push-Pull Test a Method of Evaluating Formation Absorption Parameters for Predicting the Environmental Effects on In-Situ Coal Gasification and Uranium Recovery" 1980 by Marcel Dekker, Inc.,4(3), 181-206.

(Continued)

*Primary Examiner*—Sam P Siefke (74) *Attorney, Agent, or Firm*—Grossman Tucker Perreault & Pfleger PLLC (57) ABSTRACT

In general, the purpose of the probe system is to provide improved rapid field methods using re-designed direct push technology (DPT) and "push-pull testing" concepts to evaluate in situ chemical, biochemical, surfactant, adsorptive media, and leaching and fixation remediation technologies for hazardous subsurface contaminant(s). The probe system and methods described here when applied to a hazardous waste site being considered for in situ remediation of contaminants (organic or inorganic) by the listed treatment technologies will yield information that greatly reduces the uncertainty with regards to treatment effectiveness for the in situ soil, groundwater, and contaminant(s) conditions affecting dosage requirements and reaction rate(s) for various reactants. The probe system described here is multi-purpose in that it was designed: 1) to measure the relative permeability of the subsurface soil and groundwater to a liquid or gas ejectant, 2) to recover soil gas, soil, or groundwater samples for contaminant analyses, 3) to measure the chemical dosage and reaction, dissolution, adsorption, desorption, leaching, or fixation rate of a reactant such as a chemical or biochemical oxidant, metallic or bimetallic dehalogenating agent, surfactant or emulsifier solution, adsorbent media regenerant, leaching or fixation reagent that is injected into the matrix and withdrawn during a push-pull test, 4) to perform combinations of the above, 5) to measure the in situ adsorption capacity of adsorbent media and subsequently measure the effectiveness of regenerant(s) for the adsorbent media, and (6) to measure the effectiveness of a treated soil column for inorganic contaminant(s) leaching or fixation. In addition to being an in situ remedial alternatives evaluation tool, the probe system can be used as a reactant(s) delivery device after the specific remedial technology has been selected.

9 Claims, 3 Drawing Sheets

U.S. PATENT DOCUMENTS 5,741,427 A     4/1998   Watts
6,098,448 A *   8/2000   Lowry et al. .................... 73/38
6,761,062 B2   7/2004   Shapiro

OTHER PUBLICATIONS

Field, J.A., et al., "Laboratory Investigation of Surfactant-Enhanced Trichloroethene Solubilization Using Single-Well, "Push-Pull" Tests", Department of Agricultural Chemistry, Oregon State University, vol. 37, No. 4—Ground Water—Jul.-Aug. 1999, 581-589.

Haggerty, R., et al., "Simplified Method of "Push-Pull" Test Data Analysis for Determining In Situ Reaction Rate Coefficients", Reprinted from Ground Water, vol. 36, No, 2, Mar.-Apr. 1998, 314-324.

Istok, J.D., et al., "Single-Well, "Push-Pull" Test for In Situ Determination of Microbial Activities", Reprinted from Ground Water, vol. 35, No. 4, Jul.-Aug. 1997, 619-631.

Istok, J.D., et al., "Laboratory and Field Investigation of Surfactant Sorption Using Single-Well, Push-Pull Tests", Department of Civil Engineering, Oregon State University, vol. 37, No. 4, Ground Water, Jul.-Aug. 1999, 589-598.

Istok, J.D., et al., "Single-Well "Push-Pull" Partitioning Tracer Test for NAPL Detection in the Subsurface", Environmental Science & Technology, vol. 36, No. 12, 2002, 2708-2716.

Schroth, M.H., et al., "In Situ Evaluation of Solute Retardation Using Single-Well Push-Pull Tests", 2000 Elsevier Science Ltd., 13 pages.

Schroth, M.H., et al., "In Situ Assesment of Microbial Sulfate Reduction in a Petroleum-Contaminated Aquifer Using Push-Pull Tests and Stable Sulfur Isotope Analyses", 2001 Elsevier Science B.V., 17 pages.

Snodgrass, M., et al., "A Method to Infer In Situ Reaction Rates From Push-Pull Experiments", vol. 36, No. 4, Ground Water, Jul.-Aug. 1998, 645-650.

* cited by examiner

**FIGURE 1
PROBE SYSTEM
PUSH-PULL TEST MODE**

FIGURE 2

GASEOUS REACTANT MODE

FIGURE 3

IN SITU PACKED ADSORBENT BED MODE

IN SITU REMEDIAL ALTERNATIVE AND AQUIFER PROPERTIES EVALUATION PROBE SYSTEM

BACKGROUND OF THE INVENTION

Both State and Federal government have strict regulations governing hazardous organic and inorganic contaminants in the environment. Subsurface soil and groundwater contamination with organic and inorganic contaminants has been the concern of State and Federal government since the 1970's. Action levels and clean-up standards have been promulgated by both State and Federal government for numerous organic and inorganic contaminants. Regulated organic contaminants in the subsurface environment include, but are not limited to: polychlorinated biphenyls (PCBs); chlorinated volatile organic compounds (CVOCs) such as tetrachloroethene (PCE), trichloroethene (TCE), trichloroethane (TCA), dichloroethene (DCE), vinyl chloride; fuel constituents such as benzene, ethylbenzene, toluene, xylene, methyl tert butyl ether (MTBE), tertiary butyl alcohol (TBA), polynuclear aromatic hydrocarbons (PAHs), ethylene dibromide (EDB); pesticides such as (but not limited to) DDT; herbicides such as (but not limited to) silvex. Regulated inorganic contaminants in the subsurface environment include, but are not limited to: heavy metals, such as lead, arsenic, chromium, mercury, silver. The State and Federal regulations that govern these subsurface contaminants outline a protocol for subsurface investigation to identify the extent of contamination, identification of the human health and ecological risk posed by the contaminants, development of remedial action alternatives for reducing or eliminating any significant risk posed by the contaminants, and selection and implementation of remedial measures to achieve the remediation goals.

One method of subsurface investigation used to rapidly delineate the extent of hazardous organic and inorganic contaminants is known as direct push probe technology or direct push technology (DPT). Typically, this technology is used to assess organic contaminants in soil gas, soil, sediment, or groundwater. It is also used to assess inorganic contaminants in soil, sediment and groundwater.

DPT uses a vibratory percussion or slide hammer or pneumatics to advance a small diameter probe or push rod ranging from approximately 1 inch to 4-inch outside diameter into the soil and/or groundwater. DPT is typically mounted: 1) to a vehicle to be mobile, 2) to a support frame so that it can be moved inside a building for sub-slab investigation, or 3) to a boat or barge for evaluation of contaminants in sediment underlying a water body. DPT has been in existence since the late 1980's in the environmental investigation field as a means to rapidly collect soil, soil gas, and groundwater samples for contaminant analysis. DPT was much faster and cost effective as compared to conventional drilling methods using hollow stem augers or drive and wash casing advancement. Geoprobe Systems, Inc. and Simco Drilling Equipment, Inc. have emerged as leaders in the manufacture of DPT, among other competitors such as HydroPunch. Since the late 1980's most of the development effort in DPT has gone into geologic and contaminant investigative techniques to identify the soil type and contaminant(s) present in soil, soil gas, and groundwater. For example, there are probe techniques for collecting soil samples, soil gas samples, groundwater samples, identifying the soil lithology through electrical conductivity and cone penetrometer sensors. The American Society of Testing Materials (ASTM) has recently published a guidance document on the use of direct push technology for environmental investigations (D6724 Standard Guide for Selection and Installation of Direct Push Ground Water Monitoring Wells).

PRIOR ART

Improvements in subsurface sampling equipment such as that identified in U.S. Pat. No. 5,487,431 provide the means to pump out large samples of strata water or gas and collect samples on the top of rock layers. More recently, there has been technical advancements with in situ probe techniques for determining aquifer properties, such as vertical profiling of hydraulic conductivity, as described by Cho, Wilson, and Beck (2000). Other investigators (U.S. Pat. No. 5,548,991) have developed a general purpose probe concept for relative permeability testing of earthen material that could be used in many fields, such as agriculture, hydrology, and others. Still other investigators have developed downhole investigative techniques for evaluating aquifer properties in a bedrock aquifer (patent application Ser. No. 09/729,791) whereby an assembly of equipment is lowered into an open borehole in bedrock. It has become common technical practice to perform hydraulic conductivity profiling of saturated aquifers using DPT. It is less common and more difficult to perform hydraulic conductivity profiling in bedrock aquifers for several reasons; one being that DPT is not currently capable of penetrating into bedrock. The concept of relative permeability has not been used in environmental investigations as an economical means of evaluating aquifer properties. Only hydraulic conductivity has been used. However, relative permeability correlates to hydraulic conductivity and has the advantage of yielding continuous permeability information in less time. During the relative permeability testing for environmental investigations a small volume of liquid or gas is used as an ejectant so as not to mobilize any contaminants.

Another relatively new concept in the environmental field known as "push-pull testing" using a single or two probes or wells offers an improved method for in situ evaluation of subsurface reactions with hazardous contaminant(s) over traditional bench testing or pilot testing. The traditional approach for evaluation of the ability of a reactant to react with a subsurface contaminant involves either a bench-test in a laboratory with a limited number of subsurface soil and groundwater samples collected from the area of contamination or a pilot-test whereby one monitoring well(s) is installed for the injection of the reactants and several other monitoring wells surrounding the injection well(s) are also installed for monitoring of contaminant concentration both pre and post reactant injection into the aquifer. Push-pull testing used to assess in situ reaction rates consists of two stages. In the first stage, the "push", a well mixed slug of two (or more) completely mixed solutes is injected rapidly into the groundwater through a single probe or well. One of the solutes is conservative and is only subjected to advection and dispersion. The other solute is presumed to be degrading irreversibly. The background concentrations of the solutes are assumed to be negligible. After the injection, the "pull" stage begins. Groundwater is extracted periodically from the probe or well and the concentrations of the two solutes are measured over time.

In the mid 1990's, push-pull testing that was originally developed in the oil industry has been used in the environmental remediation field to evaluate: 1) in situ reaction rates for induced biostimulation of microbes for the biodegradation of subsurface contaminants, 2) surfactants ability to solubilize contaminants adsorbed to soil into the groundwater for recovery, and 3) the recovery potential of non-aqueous liquids (NAPLs), such as oil, from subsurface soil. Most push-pull testing has been done using monitoring wells, although the literature does indicate that testing has also been done using conventional probe technology unlike that specified here.

Just as technology has advanced in regards to subsurface investigation practice for organic and inorganic hazardous contaminants, so has the technology used for remediation of these subsurface hazardous contaminants. Since the mid 1990's, in situ chemical oxidation using such oxidants as hydrogen peroxide, Fenton's reagent, modified Fenton's reagent, permanganate, persulfate, ozone, and mixtures of these, has grown to become a more accepted technology used for the in situ destruction of various organic contaminants such as PCBs, CVOCs, and fuel constituents mentioned previously. In addition, certain metallic and bimetallic nanoparticles have been shown to have dehalogenating capability for some chlorinated organics. Several patents have been issued in regards to in situ chemical oxidation as a remediation technology.

Some chemical oxidants, such as hydrogen peroxide, and Fenton's reagent, can produce rapid exothermic reactions with the organic contaminants previously mentioned whereby a significant amount of heat and pressure is released as the reaction occurs. More recently, Fenton's reagent has been modified to include chelated iron catalyst so as to moderate the reaction (U.S. Pat. No. 5,741,427) and extend the life of the hydroxyl radical involved with the decomposition of the contaminant(s). This modified Fenton's reagent can be applied using conventional DPT by injecting the chemical reactant(s) into the aquifer from the screened portion of a conventional direct push probe. However, relative permeability or push-pull testing of these reactant(s) from a probe or otherwise is not a part of the prior art.

More recent patent applications involving in situ chemical oxidation focus on provision of in situ bimetallic nanoparticles for dehalogenation of CVOCs and provision of carrier compounds to assist with transport of bimetallic nanoparticles in the subsurface, so as aid with distribution of the nanoparticles to the contaminant(s).

Other areas of in situ remediation practice have focused on the use of surfactants and cosolvents, such as alcohols to desorb contaminants that were adsorbed to subsurface soil. Once desorbed, these contaminants are solubilized in the groundwater and some means of groundwater recovery is provided. For those contaminants that are not easily desorbed and solubilized by surfactants or cosolvents, such as NAPLs, partitioning tracers have been used to preferential adsorb to the NAPL so that the amount of NAPL in the subsurface can be quantified.

A most recent area of research in the field of in situ remediation involves the use of in situ adsorbent media to adsorb subsurface contaminants from the groundwater thereby limiting their migration and re-concentrating them. Once the contaminants are adsorbed to an adsorbent media, such as activated carbon or natural zeolites, the adsorbent media must be either replaced or regenerated in situ to allow for continued adsorption. Chemical oxidants have been proposed for destruction of the adsorbed contaminants and replenishing of the adsorption sites on the media.

With all of these recent developments, the prior art does not reference the use of DPT in the environmental field for: 1) relative permeability testing, 2) push-pull testing of chemical reactants for the purpose of in situ chemical oxidation evaluation testing, 3) push-pull testing of gaseous reactant(s) or gaseous/liquid reactant mixtures, 4) evaluation of in situ packed bed adsorbent regeneration, 5) evaluation of in situ soil column chemical oxidation testing, or 6) in situ evaluation of fixation or leaching of inorganics from soil columns.

Additionally and specifically, the contemplated probe system of this current invention differs from the generalized permeameter probe described by Ritson (U.S. Pat. No. 5,548,991) as follows: 1) it contains either horizontal or vertical slots on the periphery to be used as exits and inlets for fluids or gases as opposed to ports, 2) there is no expanded section of the probe which is advantageous for driving the probe to greater depths as required in environmental investigations, 3) it is designed to be driven by existing DPT, 4) it is fitted with a pressure transducer and temperature sensor to monitor the changes in pressure and temperature of the fluids or gases as necessary during a relative permeability test or push-pull test and the signals are input into a data acquisition unit for storage and display. Finally, the probe is specifically designed for rapid in situ evaluation of remedial alternatives for subsurface contamination, as opposed to general purpose relative permeability. It is highly advantageous that the relative permeability can be determined from the same probe as a push-pull test, because the subsurface contaminant(s) are most likely to follow the subsurface path of least resistance to flow that correlates to the subsurface path with the greatest relative permeability. It is most likely the location with the highest relative permeability where one could trace the path of contaminant migration or find the greatest contaminant concentration(s). With the relative permeability and contaminant concentration, one is able to select the useful location for performing a push-pull test(s).

The probe system differs from the device described by Shapiro (U.S. patent application Ser. No. 09/729,791) which is designed for insertion in an open borehole in rock. Also, the probe described here has a small enough diameter that it can be placed in an existing 2 inch diameter or greater monitoring well with a packer around the probe to seal the surface.

The probe system differs from the existing probes offered by GeoProbe Systems, Inc., Simco Drilling Equipment, Inc. and others, because it can be used to perform relative permeability, and push-pull tests using the three modes shown in the Figures, while also providing for ejection of a probe hole sealant.

The probe system differs from that described by Webb (U.S. Pat. No. 5,487,431) in both purpose and design. The purpose of the probe device of this patent is for sampling only, and it uses a retractable slotted section.

The prior art describes push-pull testing using biochemical reactants for biostimulation and using surfactants for contaminant recovery. The prior art does not describe push-pull testing in combination with relative permeability testing using any type of probe alone or as a multi-purpose probe. The prior art does not describe push-pull testing for chemical oxidants, such as Fenton's reagent, modified Fenton's reagent, ozone, permanganate, persulfate, or combinations thereof; nor metallic or bimetallic nanoparticles, for remediation of contaminants. The prior art does not describe push-pull testing for the in situ evaluation of gaseous reactants, regeneration of adsorbent media, or the efficacy of leaching and fixation reagents for treating a soil column. The prior art does not describe the measurement of temperature in pressure during a push-pull test to evaluate the chemical reaction occurring. The prior art only describes pilot testing of chemical oxidants whereby a chemical oxidant is injected into the ground, but not withdraw from the same probe, borehole, or well.

SUMMARY OF THE INVENTION

The present invention performs relative permeability profiling in lieu of hydraulic conductivity profiling, because it is faster and more easily automated than hydraulic conductivity testing while yielding information about likely stratigraphy and contaminant migration pathways. During relative permeability testing with DPT, the present invention ejects a sealant from the probe above the chamber from which the ejectant exits to direct it into the formation and prevent it from traveling upwards along the probe body towards the ground surface. The present invention can also eject a lubricant from the same chamber to aid in driving the probe to a greater depth.

The present invention performs in situ push-pull testing for chemical, biochemical, surfactants, adsorbent media regenerant, leaching or fixation agents using direct push probe technology as opposed to monitoring wells, because of the reduced time and cost of pneumatically advancing a probe using direct push technology as opposed to installing a monitoring well use conventional drilling. This is particularly apparent if multiple locations on a hazardous waste site will be evaluated using the probe described here. During push-pull testing of a chemical reactant, particularly one undergoing an exothermic reaction, it would be advantageous to eject a sealant from the probe above the chamber from which the reactants are injected and withdrawn during the push-pull testing, so as to contain the heat and pressure from the exothermic reaction. The prior art does not accommodate ejection of a sealant from a probe prior to performing a push-pull test. The prior art does describe the use of a conventional direct push probe lowered into an existing monitoring well while using an inflatable packer in the well to make a seal between the probe body and the inside of the monitoring well above the point of injection and withdrawal of reactant(s).

The present invention uses a direct push probe to evaluate in situ a gaseous reactant(s) or gaseous/liquid mixture of reactant(s) in a push-pull test for chemical or biochemical oxidation of contaminant(s).

The present invention uses a direct push probe to evaluate the in situ ability of adsorbent media to adsorb contaminants from the groundwater, and it is used to evaluate the ability of regenerants to degrade contaminants adsorbed to the media as well as replenish adsorption sites on the media.

The present invention uses a direct push probe to evaluate in situ soil column chemical oxidation testing for degradation of organic contaminants in soil column samples.

The present invention uses a direct push probe to evaluate the efficacy of a reagent for in situ fixation or leaching of organic or inorganic compounds from a soil column sample.

The in situ remedial alternatives and aquifer properties evaluation probe system that is presented here is a multi-purpose probe system used to measure relative permeability of soil and groundwater with depth in lieu of hydraulic conductivity, contaminant concentrations in soil vapor, soil, or groundwater with depth, and to measure the effectiveness of reagents, or surfactants during a push-pull test. The probe allows for the collection of the most significant information from one probe relative to evaluating in situ remedial alternatives for contaminant remediation. Instead of using multiple probe devices as described in the product literature of GeoProbe Systems, Inc., Simco Drilling Equipment Inc., and others, all relevant information that pertains to the in situ application of chemical oxidants, biochemical reactants, surfactants, adsorbent media regenerants, leaching or fixation agents to the subsurface for remedial alternatives evaluation can be rapidly collected from a single probe system using one of three modes. This data includes relative permeability profile with depth, contaminant concentration profile with depth, and the in situ chemical dosage requirements compared to depth, relative permeability, and contaminant concentration.

The probe system can measure relative permeability of soil and groundwater below ground surface by measuring continuously or incrementally at discrete intervals the flow of fluid or gas ejected from the probe as the probe penetrates the subsurface at a continuous rate. Current practice is to measure in situ hydraulic conductivity as described by Cho, et al, at discrete intervals, which is more time consuming and costly, while producing less useable data relevant to the application of reactants or surfactants for remediation of subsurface contaminants. After the relative permeability of the subsurface is measured with depth, the probe can be withdrawn and either moved to a nearby position (assuming that a sealant was used during the relevant permeability testing that would make it impossible to reuse the same probe hole) on the surface or the probe hole reused, if a sealant was not required during the relative permeability test, whereby it is advanced to the desired depth depending on the relative permeability information collected. At this depth a vapor, soil, or liquid sample is withdrawn and analyzed for the desired contaminant(s) to determine their presence or absence. Then, a push-pull test as described by Istok, et al, can be performed by injecting a reactant or surfactant solution with a conservative tracer and withdrawing the reactant or surfactant solution. The amount of tracer and injected reactant or surfactant species is measured with time to produce a curve during the injection and withdrawal. From this curve a mass balance on the conservative tracer is performed to evaluate whether all of the reactant surfactant solution that was injected has been withdrawn. From the concentration in reactant species over time, a reaction rate can be determined.

The push-pull test can be performed at more that one depth in the same probe location as desired depending on the contaminant concentration and/or relative permeability. One reason to do this would be to assess relative permeability losses due to in situ chemical oxidation. The literature describes metal precipitation of manganese that can occur during chemical oxidation with permanganate in the subsurface that results in a loss of permeability. The push-pull test can be conducted in the same location a second time using only a tracer to evaluate losses in relative permeability due to chemical oxidation. Losses in permeability of the soil may be an undesired effect of chemical oxidant application or in some cases an intended effect.

DPT is typically mounted: 1) to a vehicle to be mobile, 2) to a support frame so that it can be moved inside a building for sub-slab investigation, or 3) to a boat or barge for evaluation of contaminants in sediment underlying a water body. The probe described here can be one of several diameters ranging from approximately 1 inch to 4 inch outside diameter depending on the power available to advance the probe into the subsurface to the desired depth. The probe device can be configured for in situ relative permeability testing, push-pull testing mode, gaseous reactant testing mode, and in situ packed adsorbent bed or soil column testing mode. For relative permeability testing, the probe system is configured to advance the probe at a constant rate while ejecting a fluid or gas at a constant flow rate with the simultaneous measurement of the change in pressure of the fluid or gas. For push-pull testing mode, the probe system is configured to control the flow rate and pressure of reactant, reactant/surfactant solution, leaching or fixation agent, during injection and withdrawal while also monitoring the temperature of the reactant, reactant/surfactant solution, leaching or fixation agent. In this mode of operation, the selected reagent is injected into the soil and/or groundwater and withdrawn from the soil and groundwater through the same slots in the lower chamber of the probe. For the gaseous reactant mode, a gaseous reactant (s) or gaseous/liquid reactant mixture is injected into the soil and groundwater from the slots in the lower chamber, mixes with the soil and groundwater while rising due to buoyancy forces, then groundwater containing the reacted gas and by-products is withdrawn from slots in an upper chamber. For in situ packed adsorbing bed mode, the packed bed section is filled with the adsorbent media of interest and the probe is placed below the groundwater table to allow saturation of the adsorbent media with contaminated groundwater. Groundwater is then drawn upwards through the adsorbent media and through a sampling tube to the ground surface by a pump for sampling and analyses. In the case where an adsorbent media is tested, the adsorbent media reaches saturation after some period of time. The adsorbent media is then regenerated by passing a regenerant through the media and collecting the spent regenerant and media for contaminant analyses. Regeneration of the adsorbent media in the packed bed section is similar to performing a "mini" push-pull test in a confined space on an adsorbent or soil column and it is analyzed as such with a few mathematical modifications to the analysis. For in situ soil column testing using the in situ packed adsorbent bed mode, the packed bed section is filled with an undisturbed soil sample collected from an adjacent bore hole in the area of contamination. Groundwater is then drawn upwards through the soil column and through a sampling tube to the ground surface by a pump for sampling and analyses. When equilibrium is reached with regards to the amount of contaminant adsorbed to the soil column, the pump is stopped. The soil column is injected with a reagent and reacted, and then the reacted solution is withdrawn to simulate a "mini" push-pull test on the soil column sample containing contaminant (s). For in situ soil column testing of precipitation or fixation the packed bed section is loaded with a treated and preferably undisturbed soil column sample that has been treated with a leaching or fixation agent. It is then lowered into the groundwater and allowed to contact the groundwater as with the adsorbent media. After some period of time, the groundwater within the soil column is withdrawn and analyzed for select constituents.

Relative permeability of subsurface soil and groundwater is measured by advancing a probe into the ground at a constant rate while simultaneously ejecting a biodegradable fluid sealant, and vapor or liquid, from the probe to the soil and groundwater. The relative permeability of the soil and groundwater is determined by measuring either changes in flow rate at constant pressure or changes in pressure at constant flow rate of the ejected gas or fluid. The prescribed method of operation of the probe seals the probe hole allowing collection of discrete liquid or vapor samples.

In addition, the rate of advance of the probe can be stopped, and the push-pull testing mode used to evaluate the in situ chemical or biochemical reaction rate, or adsorption-desorption rate of an injected reactant or surfactant is measured by first injecting a reactant or surfactant solution through the tip of the probe allowing the reactant or surfactant to react or adsorb-desorb for a certain amount of time, and then withdrawing the reacted solution. The reactant or surfactant solution contains a conservative tracer, such as bromide, a chemical reactant such as Fenton's reagent, modified Fenton's reagent, ozone, persulfate, permanganate, metallic or bimetallic (such as, but not limited to, iron and platinum) nanoparticles with or without a nanoparticle carrier compound(s), combinations of these or, a biochemical reactant such as nutrient or a biological substrate, or a surfactant. For non-aqueous phase liquid recovery evaluation testing, a partitioning tracer can be injected and withdrawn from the soil and groundwater with the probe in push-pull testing mode. In the gaseous reactant mode, the probe is used to evaluate the reaction of a gaseous reactant or gaseous reactant mixture, such as but not limited to ozone or ozone/air mixture or pure oxygen, with the soil and groundwater contaminant(s). In the in situ adsorbent media mode, the probe is used to evaluate the ability of an adsorbent to adsorb contaminant(s) from the groundwater and then the ability of a regenerant to regenerate the media. In this same mode, the probe can also be used to evaluate chemical oxidation of contaminant(s) in a soil column. Also, the probe can be used to evaluate the fixation or precipitation of inorganics from a soil column sample. Typically, the probe is used in one mode by interchanging sections of the probe.

The data acquisition system monitors the flowrate, pressure, and temperature of ejectant fluids or gases during the relative permeability test. It also monitors the flow rate, pressure, and temperature of reactants or surfactants during the injection phase and withdrawal phase for push-pull testing mode, gaseous reactant mode, and in situ packed adsorbent media mode. The overall probe system includes a rate of probe advance monitoring and controlling device, holding tanks for the fluid used for the relative permeability and push-pull tests, fluid pumps, a pressure regulator, flow meters, a water level indicator, a pressure transducer and temperature sensor located in the probe, power source and a computer interface. The probe system can be used to measure ambient hydraulic pressure, fluid or gas volume, pressure, and temperature during ejection for the purpose of inferring relative permeability, soil vapor, soil or groundwater sample collection for contaminant analyses, or for performing testing in one of three modes (push-pull test, gaseous reactant, or in situ adsorbent media mode). The probe system does not usually require a prior borehole, although in some cases it may be necessary to auger through soil containing cobble. Then, the probe device is pushed into and withdrawn from the ground using existing DPT, which has the capability the drive a probe to depths of greater than 100 feet below ground surface under the right soil conditions.

DETAILED DESCRIPTION OF THE PREFERRED EMBODIMENT

The probe system described here is multi-purpose in that it was designed: 1) to measure the relative permeability of the subsurface soil and groundwater to a liquid or gas ejectant, 2) to recover soil gas, soil, or groundwater samples for contaminant analyses, 3) to measure the chemical dosage and reaction, dissolution, adsorption, desorption, leaching, or fixation rate of a reactant such as a chemical or biochemical oxidant, metallic or bimetallic dehalogenating agent, surfactant or emulsifier solution, adsorbent media regenerant, leaching or fixation reagent that is injected into the matrix and withdrawn during a push-pull test, 4) to perform combinations of the above, 5) to measure the in situ adsorption capacity of adsorbent media and subsequently measure the effectiveness of regenerant(s) for the adsorbent media, and (6) to measure the effectiveness of a treated soil column for inorganic contaminant(s) leaching or fixation. In addition to being an in situ remedial alternatives evaluation tool, the probe system can be used as a reactant(s) delivery device after the specific remedial technology has been selected. Specifically, it can be used to perform relative permeability, and push-pull tests using the three modes shown in the Figures, while also providing for ejection of a probe hole sealant. Relative permeability correlates to hydraulic conductivity and has the advantage of yielding continuous permeability information in less time than hydraulic conductivity testing. Push-pull testing is an in situ test procedure used to evaluate aquifer properties, such as groundwater velocity and porosity, and the capability in terms of dosage and reaction rate of a chemical or biochemical reactant for degrading contaminant(s) attached to soil or dissolved in groundwater. In addition, push-pull testing as performed with the probe system here can be used to evaluate gaseous reactants or the adsorbing capacity of an in situ adsorbing media (or soil column) and its subsequent regeneration capacity by performing a "mini" push-pull test. The probe system is also used to evaluate in situ inorganic contaminant leaching or fixation to soil or other media.

The probe system performs in situ push-pull testing for chemical or biochemical reactant(s) using DPT as opposed to monitoring wells, because of the reduced time and cost. During push-pull testing of a chemical reactant, particularly one undergoing an exothermic reaction, it would be advantageous to eject a sealant from the probe above the chamber from which the reactants are injected and withdrawn during the push-pull testing, so as to contain the heat and pressure from any exothermic reaction. The probe system uses a direct push probe to evaluate in situ a gaseous reactant(s) or gaseous/liquid mixture of reactant(s) in a push-pull test for chemical or biochemical oxidation of contaminant(s).

The probe system uses a direct push probe to evaluate the in situ ability of adsorbent media to adsorb contaminants from the groundwater, and it is also used to evaluate the ability of regenerants to degrade contaminants adsorbed to the media as well as replenish adsorption sites on the media. The probe system uses a direct push probe to evaluate in situ soil column chemical, or biochemical oxidation testing for degradation of organic contaminants in soil column samples; as well as surfactant dissolution of contaminants from soil columns. The probe system uses a direct push probe to evaluate the in situ fixation or leaching of organic or inorganic compounds from a soil column sample.

The preferred embodiment of this probe system is typically mounted: 1) to a vehicle to be mobile, 2) to a support frame so that it can be moved inside a building for sub-slab investigation, or 3) to a boat or barge for evaluation of contaminants in sediment underlying a water body. The probe described here can be one of several diameters ranging from approximately 1 inch to 4 inch outside diameter depending on the power available to advance the probe into the subsurface to the desired depth. The probe system can be configured for in situ relative permeability testing, push-pull testing mode, gaseous reactant testing mode, and in situ packed adsorbent bed or soil column testing mode.

The preferred embodiment of this invention comes in three modes: the push-pull test mode, the gaseous reactant mode, and the in situ packed adsorbent bed or soil column mode. Each mode will be described in turn below.

Push-Pull Test Mode

Figure 1:
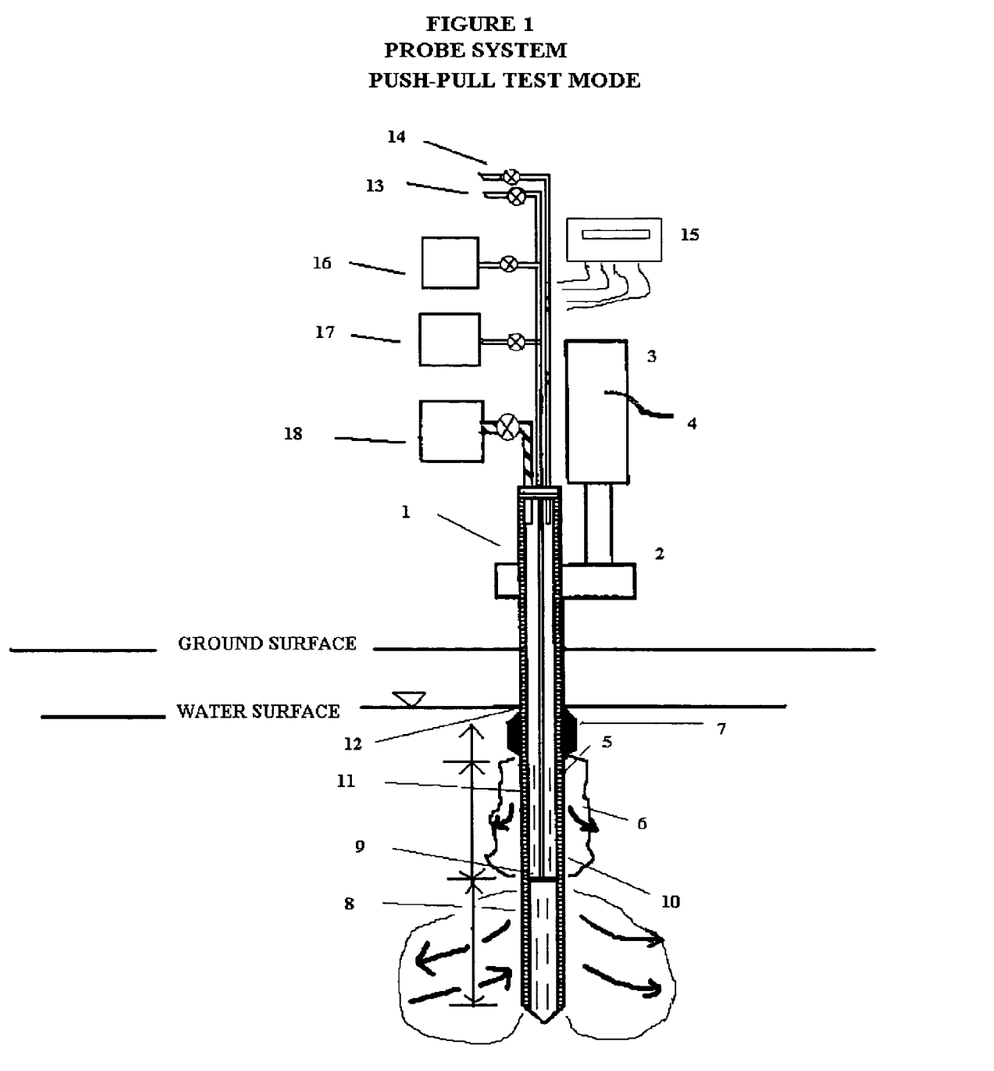
FIG. 1 presents a sectional view of the probe in push-pull test mode.

In FIG. 1, the probe system is presented in a sectional view when in the push-pull test mode used with liquid-based reactant(s) as opposed to gaseous reactants. The probe system (1) is mounted to a vehicle, support frame, or boat/barge (2) and uses existing DPT whereby a vibratory percussion hammer (3) with a (4) constant advance rate controller pushes the probe of approximately 1 inch to 4 inches outside diameter into the ground at a constant rate of advancement. The probe has either horizontal or vertical slots around its periphery (5) to allow for ejectants (6) to exit the probe or for extractants to enter the probe. The probe can contain a short expanded section (7) of approximately 2 inches in length to reduce upward flow of ejectants around the exterior of the probe. The probe end is separated into two slotted chambers with the lower chamber (8) to be used for ejection of a liquid or gas at constant flow rate or constant pressure during a relative permeability test as the probe is advanced. Fluids or gas flows into or out of the lower chamber from an injection line connected to a plate with a tubing connector (9). At location (10) in the probe body, a solid riser section can be inserted to separate the lower chamber from the upper chamber or a packed bed section can be inserted to replace the upper chamber. The upper chamber (11) is used for ejection of a sealant, such as (but not limited to) a bentonite slurry or a polymer, to form a seal against fluid flow upwards towards the ground surface along the probe body. The probe body above the upper chamber is solid riser (12). The tubing connected to the lower chamber rises to the ground surface through the probe body, and attaches to a primary sample collection or injection system comprising valves, pumps, and tanks (13). There is also a secondary sample collection or injection system connected to the top of the probe body (14). During relative permeability testing, the change in pressure for a constant flow rate system or the change in flow rate for a constant pressure system is measured using a pressure transducer and flow meter, and subsequently stored in a computer data acquisition unit (15). The changes in either pressure or flow rate are used to assess the relative permeability with depth from ground surface. The reagent solution reservoir (16) contains the chemical, biochemical reactant(s), or surfactant(s) (but not limited to) and a pumping system with a pressure gauge and a flow meter to discharge at specified flow rate and pressure of at least 5 psi and greater depending on the soil formation pressure. The fluid or gas reservoir (17) can contain (but not limited to) ozone, air, pure oxygen, carbon dioxide, nitrogen and phosphorus containing gases, or mixtures thereof. The sealant or lubricant reservoir (18) contains the sealant and/or lubricant and a pumping system. Sealant can be ejected as the probe is withdrawn to fill the hole left by the probe as it is removed from the ground.

As used in the manner described above, the probe characterizes the relative permeability of the soil and groundwater to either liquid or gas continuously or at discrete intervals. Specifically, the relative permeability to a liquid or gas in the unsaturated zone (above the groundwater table) or in the saturated zone (below the groundwater table) can be measured.

A secondary use of the probe is to profile the contaminant concentration with depth by withdrawing a soil gas, soil, or groundwater sample from the lower chamber, and subsequently analyzing it on-site with a gas chromatograph or a similar instrument. To collect a soil sample, the lower chamber of the probe is replaced with a soil sampling tube containing an inner sleeve to hold the soil sample in a manner similar to conventional DPT soil sampling.

A third use of the probe is for performing "push-pull tests" as described in the literature by Istok, et. al. used for evaluation of in situ bioremediation and surfactant recovery of contaminant(s), as well as groundwater velocity and porosity determination. The literature does not discuss the use of pushpull tests for evaluation of chemical oxidation of contaminants. The probe is advanced to the desired depth based on relative permeability or contaminant concentration that was measured as the probe was advanced. During a push-pull test, a sealant is ejected from the upper chamber into the surrounding ground. Then, a liquid or gas solution containing a conservative tracer is ejected from the lower chamber and pushed into the surrounding ground. Then it is withdrawn and the reactant or surfactant concentration and conservative tracer measured with time until all of the liquid or gas is recovered. Push-pull testing can only be performed with liquids in the saturated zone. The recovery of gases or liquids in the unsaturated zone from a single probe cannot be adequately accomplished for analysis.

A fourth use of the probe is to perform combinations of the three uses described above from the same probe location. In addition to being an in situ remedial alternatives evaluation tool, the probe can be used as a reactant(s) delivery device after the specific remedial technology has been selected.

Gaseous Reactant Mode

Figure 2:
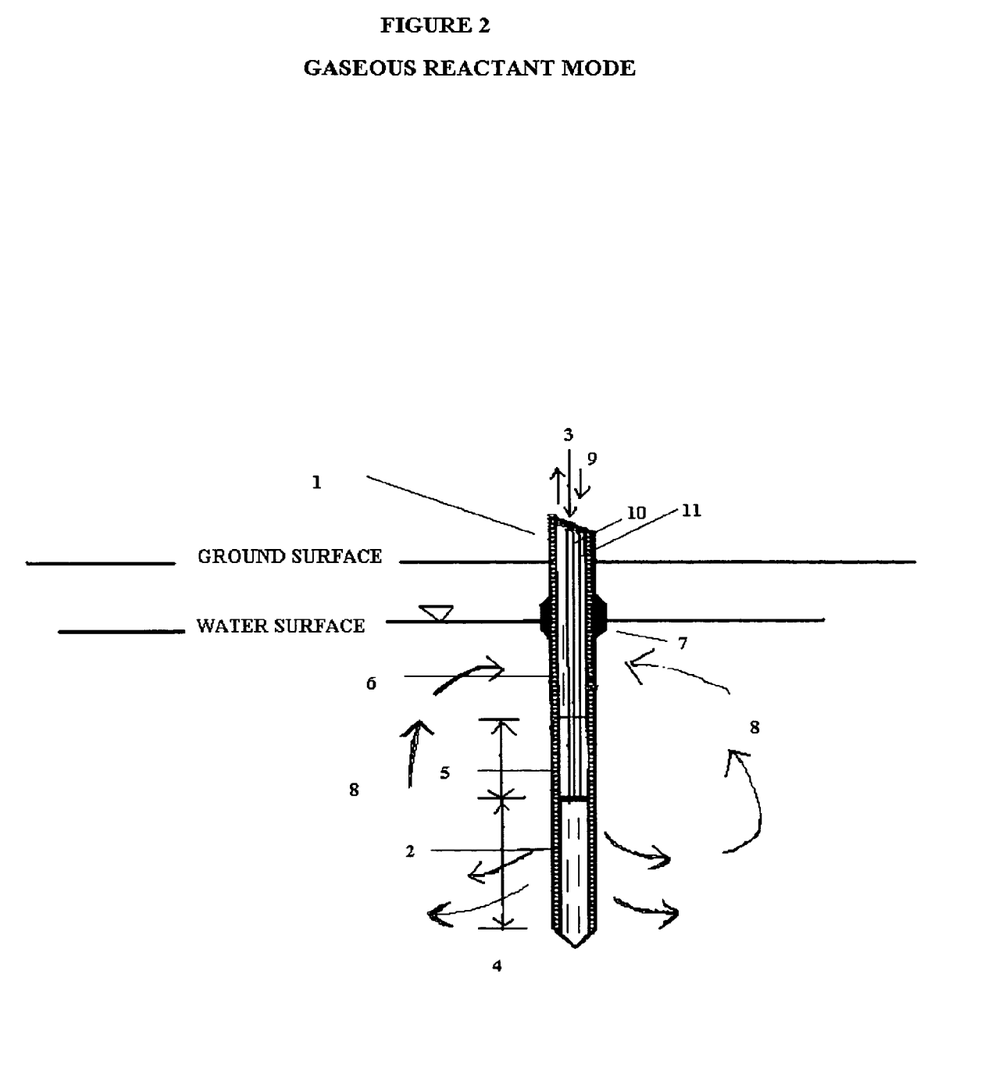
FIG. 2 presents a sectional view of the probe in gaseous reactant mode.

In FIG. 2, a sectional view of the probe system is shown when in gaseous reactant mode for use with gaseous reactant (s) or a gaseous/liquid mixture of reactant(s). The probe system (1) is advanced into the ground as described in the previous section. The probe is outfitted with a slotted lower chamber having either horizontal or vertical slots (2) for release of gaseous reactant(s) (3) into the groundwater (4) affixed to a solid riser section (5) and a slotted upper chamber having either horizontal or vertical slots (6). There is an expanded section of the probe (7) above the slotted section to reduce the upward flow of gases around the exterior of the probe. The dissolved gaseous reactant(s) (8) and reacted contaminant(s) are circulated in the groundwater by withdrawing groundwater (9) from the upper chamber. The dissolved gaseous reactant(s) enter the probe through an inner tube (10) connected to the lower chamber while the withdrawn groundwater (using an aboveground re-circulating pump) exits the upper chamber of the probe in the space between the inner tube and the probe outer body. The groundwater is re-injected through a second tube (11) connected to the lower chamber.

In Situ Packed Adsorbent Bed Mode

Figure 3:
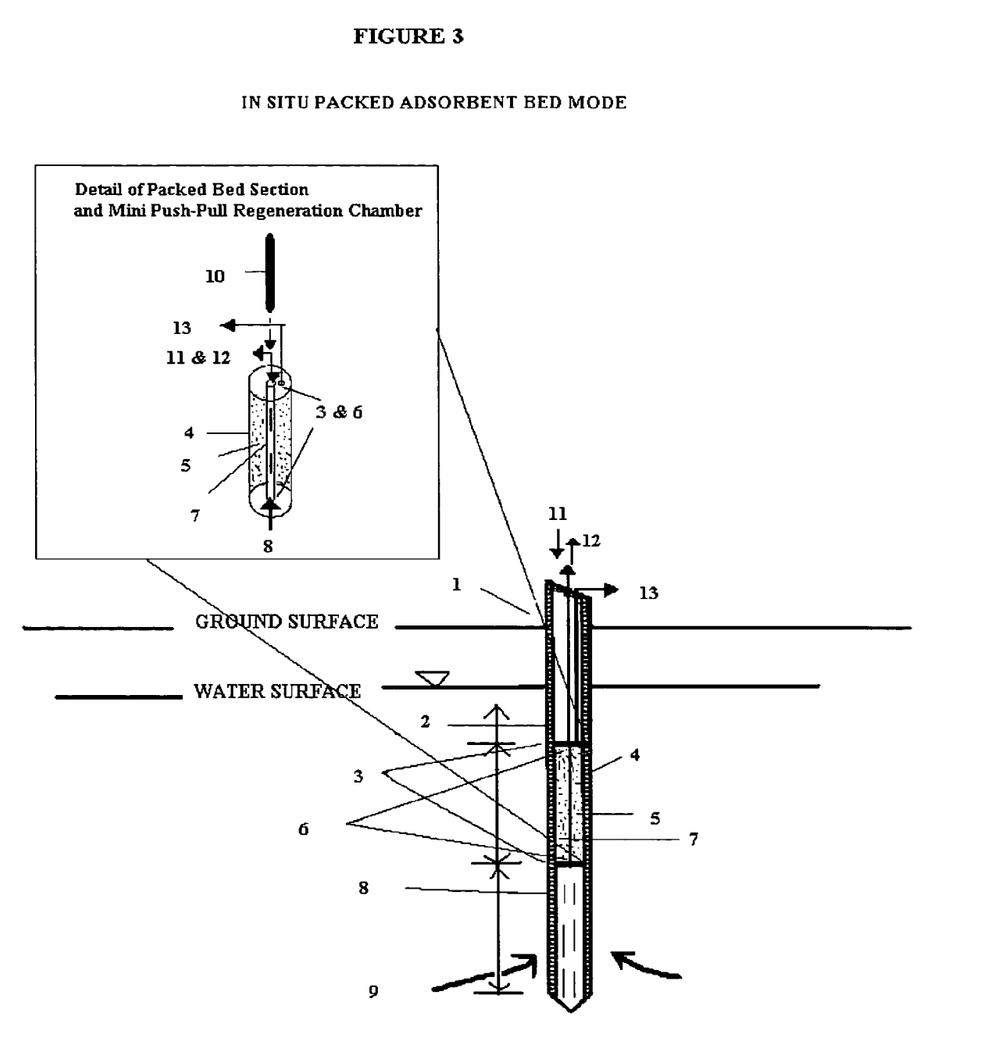
FIG. 3 presents a sectional view of the probe in situ packed adsorbent bed mode with a detail of the packed bed section and "mini" push-pull regeneration chamber.

In FIG. 3, a sectional view of the probe system is shown when configured for in situ packed bed adsorbent media mode for use with either submerged adsorbent media or a soil column sample and chemical reactant(s), surfactants, biochemical reactants, or leaching and fixation agents. With a soil column placed in the media section, either organic or inorganic treatment of the contaminants in soil can be tested. If organic contaminants in soil are to be tested, a chemical reactant(s), surfactants, or biochemical reactants are used. When inorganic contaminants in soil are to be either leached or fixed to the soil or some other media, other reagents are injected/extracted. The probe system (1) is advanced into the ground as described in previous sections. The probe is outfitted with a solid riser (2) followed by a media support plate (3) located at the top and bottom of a packed adsorbent bed section (4), which is filled with adsorbent media or a soil column sample (5) (preferably an undisturbed soil sample that is collected from an adjacent location within the area of contamination). Pressure actuated check valves (that open in only one direction) are positioned in fittings on the upper and lower support plates (6). In between the support plates is a slotted hollow injector/extractor guide tube (7) that is affixed to both support plates. The slotted lower chamber with either vertical or horizontal slots (8) is affixed to the packed bed section. When the probe is configured in this mode, it is lowered into the groundwater containing contaminants and groundwater (9) is allowed to enter the lower chamber and saturate the adsorbent media or soil column in the packed bed adsorbent media section. The groundwater and contaminants can not enter the solid riser section above the media section. Then, a slotted injector extractor tube (10) is pneumatically pushed into the center of the adsorbent media or soil column, which closes the check valve located at the bottom of the media section. A regenerant mixture (11) for regenerating the adsorbent media by destroying the adsorbed contaminants or by displacing them on the media is injected into media. Alternatively, a chemical, biochemical, surfactant, leaching or fixation agent can be injected into a soil column sample. The spent regenerant, chemical, biochemical, surfactant, leaching or fixation agent is reclaimed by reversing the pumping (12). A liquid or off-gas sample can be drawn through the media or soil column by (13) a sampling line and pump for analyses.

REFERENCES

1. Cho, Jong Soo, John T. Wilson, and Frank Beck. (2000). Measuring Vertical Profiles of Hydraulic Conductivity with In Situ Direct-Push Methods. Journal of Environmental Engineering. Volume 126, Issue 8, pp. 775-777.
2. B. M. Davis, Istok, Jonathan. D., L. Semprini. (2002) Push-Pull Tracer Test to Quantify Non-Aqueous Phase Liquid Contamination. Journal of Contaminant Hydrology, Vol. 58., p. 129.
3. Hall, S. H., S. P. Luttrell, and W. E. Cronin. A Method for Estimating Effective Porosity and Groundwater Velocity. Ground Water, Vol. 29, No. 2 March-April 1991.

What is claimed is:
1. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit; and
wherein said plurality of slots are vertical or horizontal and said sealant comprises a bentonite slurry or polymer.
2. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism, a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor and
a communication and data acquisition unit,
wherein said plurality of slots are vertical or horizontal and said lubricant comprises vegetable oil.

3. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor and
a communication and data acquisition unit,
wherein said plurality of slots are vertical or horizontal and said plurality of chambers further comprise: an upper chamber with a short expanded width section, and a lower chamber.

4. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit:
wherein said reactant comprises one or more of hydrogen peroxide, Fenton's reagent, modified Fenton's reagent, permanganate, persulfate and ozone;
one or more of pure oxygen and air;
or metallic or bimetallic nanoparticles containing iron, palladium or platinum, for inducing chemical dehalogenation;
or a microbial food source or nutrient containing compounds for inducing a biochemical reaction with subsurface contaminant(s) in soil, a soil column sample and/or groundwater;
or a surfactant or emulsifier for desorbing and solubilizing contaminant(s) from any non-aqueous phase liquid and/or the subsurface soil into groundwater;
or a regenerant for regenerating the adsorbent media;
or calcium phosphate for inducing contaminant leaching or fixation in a soil column sample, respectively; and
wherein said plurality of slots are vertical or horizontal.

5. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit: and
wherein said plurality of slots are vertical or horizontal and said adsorbent media comprises: a solid adsorbent media to adsorb contaminant(s) from the soil gas or groundwater wherein said adsorbent media can be regenerated.

6. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit, wherein said plurality of slots are vertical or horizontal and said plurality of chambers further comprise: an upper chamber with a short expanded width section, and a lower chamber; and wherein said probe system has two injection and/or withdrawal lines to the lower chamber whereby only one line is used when configured in the push-pull test mode and two lines are used when configured in the gaseous reactant mode.

7. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit,
wherein said plurality of slots are vertical or horizontal and said plurality of chambers further comprise: an upper chamber with a short expanded width section, and a lower chamber; and
wherein said probe system has a sampling line to the upper chamber when configured in any of three potential modes.

8. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a push-pull test from one of said plurality of chambers,
a chemical feed and injection system connected to said tubular probe shaft,
a gas or liquid sampling system or an adsorbent media or a soil column sample connected to said probe shaft,
a sensor;
a communication and data acquisition unit; and
wherein said plurality of slots are vertical or horizontal and said communication and data acquisition unit further comprises down hole wireless or non-wireless sensors or combinations thereof for monitoring of soil gas temperature, humidity, and carbon dioxide; and
for monitoring groundwater water level, pH, oxidation-reduction potential, and temperature a communications and computer interface, and a power supply.

9. A probe system comprising:
a hollow tubular steel-probe shaft of variable length and width sections,
a hollow steel drive point or optional, interchangeable, hollow steel soil sampler with plastic inner-sleeve proximally attached to the hollow tubular steel probe shaft,
a driving mechanism,
a regulating device for measuring and controlling the rate of probe advancement,
a plurality of chambers for the ejection of distinct fluids from each chamber,
a plurality of slots around the periphery of the chambers,
a sealant or lubricant for one of said plurality of chambers,
a fluid for permeability measurement,
a reactant for a pushpull test from one of said plurality of chambers
a chemical feed and injection system connected to said tubular probe shaft,
a gas or liquid sampling system or an adsorbent media or a soil column sample connected to said probe shaft,
a sensor and
a communication and data acquisition unit,
wherein said adsorbent media comprises: a solid adsorbent media to adsorb contaminant(s) from the soil gas or groundwater wherein said adsorbent media can be regenerated.

* * * * *